United States Patent [19]
Sharkins

[11] 4,015,127
[45] Mar. 29, 1977

[54] MONITORING FILM PARAMETERS USING POLARIMETRY OF OPTICAL RADIATION

[75] Inventor: Allen J. Sharkins, Lower Burrell, Pa.

[73] Assignee: Aluminum Company of America, Pittsburgh, Pa.

[22] Filed: Oct. 30, 1975

[21] Appl. No.: 627,248

[52] U.S. Cl. .............................. 250/341; 250/339; 250/349; 356/118
[51] Int. Cl.² .......................................... G01J 4/04
[58] Field of Search .......... 250/338, 339, 340, 341, 250/349; 356/114, 118, 209

[56] References Cited
UNITED STATES PATENTS

| | | | |
|---|---|---|---|
| 3,017,512 | 1/1962 | Wolbert | 250/349 |
| 3,355,980 | 12/1967 | Mathais | 356/118 |
| 3,426,201 | 2/1969 | Hilton et al. | 250/338 |
| 3,623,818 | 11/1971 | Gardner et al. | 250/341 X |
| 3,734,619 | 5/1973 | Newburgh | 356/27 |
| 3,802,778 | 4/1974 | Newburgh | 356/147 |
| 3,824,017 | 7/1974 | Gaylon | 356/118 X |

OTHER PUBLICATIONS

Fundamentals of Optics, by Jenkins and White, Chap. 24, (3rd edition, 1957).
Simple Technique for Very Thin SiO₂ Film Thickness Measurements, by Pliskin and Esch, 11 Applied Physics Letters, No. 8 (Oct. 15, 1967).

Primary Examiner—Archie R. Borchelt
Attorney, Agent, or Firm—David W. Brownlee

[57] ABSTRACT

A method and apparatus are disclosed for monitoring parameters of a film or coating by directing a beam of optical radiation at a film supported on a metal substrate at an angle to the film so as to plane polarize any radiation transmitted through the film, reflecting a portion of the radiation from the interface between the film and substrate, transmitting the radiation through a polarizing medium before and/or after it has been transmitted through the film to block any component of radiation other than that which is or will be transmitted through the film, and transducing the radiation reflected from the interface to provide an output signal which is a function of a parameter of the film.

34 Claims, 4 Drawing Figures

MONITORING FILM PARAMETERS USING POLARIMETRY OF OPTICAL RADIATION

BACKGROUND OF THE INVENTION

The instant invention relates generally to film monitoring and, more particularly, to an improved method and apparatus for optically monitoring thin films without attendant optical interference.

The apparatus and methods of the invention were specifically developed for determining parameters of thin radiation-transmissive films of material that may be formed as self-supporting sheets or as coatings on a base sheet. By way of example, a thin film of an organic material, such as polyethylene, may be formed on a relatively thick base sheet formed from metal foil. Typically, a great many metal cans, such as aluminum cans, have applied to one or more of their surfaces a protective organic resin film such as above-described. To perform their functions adequately as protective barriers, it is necessary that these films have a certain critical minimum thickness. To insure the existence of this minimum thickness, it is common practice to apply a coating in its wet state in greater than necessary amounts as a sort of safety factor. Quite obviously, the application of this excess coating is uneconomical and leads to fabrication difficulties. A characteristic of the film with which the invention is concerned is that the film formed either as a self-supporting sheet or as a coating, has specular surfaces and will be strongly reflective of radiation incident to either a first surface or second surface, including a second surface which is the interface surface between the film and an underlying base sheet. Radiation incident to the film will be reflected at the first and second surfaces and, in the case of a reflection-type measurement, the reflected component subsequently detected by electrical radiation sensors connected in a circuit to provide an output signal or readout that is indicative of the particular parameter of interest. In the case of a through transmission type measurement, the radiation sensors would be positioned at the side of the film opposite the radiation source to detect radiation transmitted through the film.

Various gauges for accurately measuring the organic coating applied to a metal substrate have been considered. However, to be truly effective, the coating thickness gauge should desirably be capable of measuring the coating immediately after application, while it is still wet, so that immediate alterations in the coating operation can be made to vary the coating thickness if necessary. Since the coating is not in a dry, handleable state for several seconds after its initial application, measurements at a point after the coating is dry would permit the production of considerable improperly coated sheet prior to detection thereof in a coating line moving at several hundred feet per minute. Further, any accurate measurement of a wet, mobile, fluid coating must omit physical contact between the measurement device and the coating. Also, to insure no interruption in production, the measurement should be made while the coated sheet is moving.

A reflection-type, dual-beam infrared measurement system for determining film thickness is disclosed in U.S. Pat. No. 3,017,512 issued to H. J. Wolbert on Jan. 16, 1962. Wolbert's apparatus relies on passing infrared radiation through a film or coating carried on a reflective surface of an opaque substrate. The incident radiation is reflected from the surface and out through the coating. Means are provided for selecting from the emitted infrared radiation a beam of light, a portion of the energy of which is absorbed by the coating due to the chemical structure thereof, and another beam of the emitted radiation whose wave length is such that none of this energy is absorbed by the coating. Wolbert characterized the partially absorbed beam as a sample beam and the non-absorbed beam as a reference beam.

Wolbert makes use of a known relationship between the absorption of radiant energy and the amount of absorptive material in the path of the radiant energy which may be characterized as follows: log of $I_0/I = kcd$ where; $I_0$ is the intensity of the reference beam striking the detector; $I$ is the intensity of the sample beam striking the detector; $k$ is a constant; $c$ is the concentration of absorptive material in the sample; and $d$ is the thickness of the sample. Wolbert has taught that while the above relationship was previously used mainly in determining the concentration of a certain substance in a sample by transmitting light through the sample of known thickness, the relationship is equally effective in determining thickness of a mobile, liquid film on an opaque but reflective substrate by passing the radiation into the coating and out again by reflecting the radiation from the substrate. Because there is a direct relationship between the thickness of a sample film and a difference between $I_0$ and $I$, the need to determine $I_0$ and $I$ separately in order to calculate $d$ is obviated.

It has been found that infrared light is particularly applicable in the method and apparatus of Wolbert inasmuch as substantially all organic compounds will absorb infrared radiation at specific frequencies within that range. The specific frequency or wave length at which the radiant energy is absorbed is a characteristic of the structure of the compound. The amount of radiant energy absorbed by the organic chemical is directly related to the quantity of absorbing chemicals in the path of the radiation.

One type of problem which occurs when measuring film thicknesses with a device such as is taught by Wolbert resides in the fact that Wolbert must chop or break up the radiation incident on the film to provide an AC output which per force must yield an average thickness determination for the whole region of the film moving past a given location in the time interval between successive pulses of light from the chopped reference and sample beams. Obviously, a particular readout may or may not provide a good indication of acceptable film thickness depending on whether or not the film being sampled is uniform.

Another problem which arises with either a through-transmission type measurement or a reflection type measurement such as is taught by Wolbert with respect to a film having specular surfaces is that there will be both first and second surface reflections which occur at the opposite surfaces of a self-supporting film or, in the case of a coated base sheet, at the respective outer or exposed surface of the film and the opposite surface at the interface of the film in the base sheet. While the first and second surface reflections produce respective signal components, these reflection components for each specific wave length suffer phase displacement, which, depending on the thickness of the film, may interfere with one another and result in an output signal which, in part, is a function of this phase displacement. With one of the beams of radiation of a wave length selected to not exhibit a characteristic absorption with respect to either the film or base sheet and the other wave length selected to exhibit a characteristic absorption as to the film, it is evident that, at certain film thicknesses, variations in relative phase displacements of the reflected components will occur due to the interference phenomenon and produce corresponding variation in the detected signals with consequent error in the measurement.

Many attempts have been made in the prior art to solve the interference problem described above and typical of the suggested solutions are those found in U.S. Pat. No. 3,631,526 issued to Donald C. Brunton on Dec. 28, 1971. Briefly, Brunton utilizes a system similar to that of Wolbert, supra, wherein, in a first aspect of his solution, Brunton directs each beam of radiation in a wide angle toward the surface of the film to be incident thereto at a relatively broad spectrum of angles rather than a single specific angle of incidence as in the case of Wolbert. This angle of incidence spectrum is selected to be of such breadth that reflection components will be added at all possible phase angles for each beam of radiation and the effect of interference between first and second surface reflection components for each beam is minimized. As a further refinement of his wide-angle technique, Brunton teaches selecting the reference and sample wave lengths to be sufficiently close together so that the relative phase displacement between the respective first and second surface reflection components will be minimal. Brunton teaches a third technique which may be utilized in combination with the wide-angle reflection technique or which may be utilized independently and which comprises the utilization of a relatively broad spectral band of wave lengths for the reference and sample radiation beams. Brunton teaches that utilization of a sufficiently broad spectral band of wave lengths will also result in the addition of reflection components at all possible phase angles with consequent minimization of interference error.

Unfortunately, prior art approaches to the problem such as that of Brunton approach the situation from the wrong end in that they seek to minimize the end effect rather than attempt to eliminate the cause, i.e., the interferring reflections.

In view of the foregoing, it is an object of the present invention to provide a method and apparatus for the elimination of optical interference in a reflective optical system.

Another object of the present invention is to provide improved infrared optical means for determining parameters of thin films or coatings.

Still another object of the present invention resides in the provision of an improved reflection-type optical method and apparatus for measuring parameters of fast moving, thin films and coatings without dependent optical interference.

Yet another object of the instant invention is to provide an improved, more accurate and simpler optical monitoring system and apparatus then heretofore available.

It is a further object of the instant invention to provide polarimetric means for blocking first surface reflection in an optical system measuring physical parameters in a moving film or coating.

A still further object of the subject invention resides in the provision of a method and apparatus for preventing optical interference and attendant error in a reflection-type optical measuring system caused by interference between light reflecting from a first surface of a film and phase displaced light from a second surface of said film.

A still further object of the present invention is to provide a method and apparatus for use in conjunction with an optical film thickness gauge of the type employing a selectively chopped infrared beam incident on, or transmitted through a thin film, for providing a continuous indication of film uniformity.

A still further object of this invention is to provide a method and apparatus for continuously monitoring the uniformity of the thickness of a thin film or coating utilizing a continuous beam of light incident on the moving film.

Yet a still further object of the present invention is to provide a method and apparatus for monitoring uniformity of a thin film or coating by reflecting a continuous beam of light from said film to a detector while preventing optical interference resulting from undesired reflection from the upper surface of said film.

SUMMARY OF THE INVENTION

The subject invention resides in an improved method and apparatus for monitoring various parameters, such as thickness and uniformity, of rapidly moving thin films or coatings. The invention relies on the fact that various thin films and coatings are selectively absorptive to particular optical wave length bands. It is contemplated to utilize a reflective technique wherein a beam of infrared radiation of a predetermined frequency or band of frequencies is caused to impinge on a moving film or coating in such a way as to be reflected to a detector from the bottom surface of the film or coating after being partially absorbed in passing through said film or coating. In order to prevent any unwanted reflection from the upper surface of the film or coating from optically interfering with reflection from the bottom surface of the film or coating, the beam of incident infrared radiation is made to impinge on the coating or film preferably at Brewster's Angle to thereby plane polarize the beam in a predetermined direction. Additionally, a polarizing medium such as a germanium optical flat may be placed between the film or coating and the detector so as to intercept the radiation reflected from the top surface of the film or coating preferably at Brewster's Angle. When the germanium optical flat is positioned as foresaid, it will prevent any radiation reflected from the top surface of the film or coating with a predetermined polarization plane from being transmitted to the detector because the germanium optical flat is positioned such that its angle of polarization is perpendicular to the plane of polarization of the reflected radiation from said first surface. To further assure that no unwanted radiation is reflected from the upper surface of the film or coating to the detector, a second germanium optical flat may be interposed between the radiation source and the film or coating so as to intercept the incident radiation preferably at Brewster's Angle. By positioning the second germanium optical flat as foresaid, little if any radiation will be reflected from the upper surface of the film or coating to the first mentioned germanium optical fl t which will promptly remove any residue.

Thus, in its broader aspect the invention resides in the elimination of unwanted reflections of light in an optical measuring system or instrument by positioning a radiation source or other component of the system such that radiation will be incident on an otherwise reflective surface preferably at Brewster's Angle to effect plane polarization of the radiation reflected from the reflective surface in a first direction and subsequently directing the reflected radiation at a polarizing material so oriented as to block the plane polarized light reflected from said surface. Alternately, a polarizing medium may be interposed between the radiation source and the reflected surface to plane polarize the light in a direction such that said light, when incident on said surface preferably at Brewster's Angle, will not be reflected therefrom. As a third alternative, a polarizing medium may be interposed between the source of radiation and the reflective surface, and also between the reflective surface and a detector with both polarizing mediums being oriented as if each were used alone and with the radiation incident on the reflective surface preferably at Brewster's Angle.

It should be understood that the physical principle underlying the applicant's invention resides in the fact that the germanium optical flat will pass radiation incident thereon at Brewster's Angle such that the plane of polariziation of the transmitted radiation will correspond to the vertical component of the incident radiation. Further, it is characteristic of the film that radiation incident thereon at Brewster's Angle will have its vertical component transmitted and its horizontal component reflected from the upper surface of the film. If the film is horizontal, it is clear that the reflected radiation will be plane polarized parallel to the reflective surface of the film. Accordingly, if the radiation incident on the film at Brewster's Angle has no component parallel to the reflective surface of the film, there will be no radiation reflected by the film. The same principle is operative, independent of whether the transmission polarizing medium is placed in the path of the incident or reflected radiation.

While the above-described generic inventive concept is applicable to a wide variety of optical instrumentation, a specific application of the foregoing concept resides in a method and apparatus for monitoring the uniformity of a thin film or coating on a moving substrate. In this embodiment a continuous beam of infrared radiation is directed onto the moving film at Brewster's Angle and the radiation selected to be of a wave length with respect to which the film is absorptive. A portion of the radiation incident on the film is reflected from the lower surface thereof to a detector which provides an output signal which is a function of the amount of radiation absorbed by the film which in turn is a function of the uniformity of the thickness of the film. Transmission polarizers are placed in the path of either the incident radiation, the reflected radiation or both in accordance with the aforementioned teachings to block any unwanted reflection from the upper surface of the film. Because the film is not perfectly uniform and is moving with respect to the radiation source, the light reflected from the interface between the substrate and film will vary in intensity as a function of film uniformity, and will not be masked by the overriding effect of interference typically found in 50–150 microinch thick organic films when short wave length infrared radiation is used. A moving non-uniform film functions to chop the continuous incoming radiation to provide an AC output signal which becomes the indication of non-uniformity. A uniformity monitoring system such as above described may be used either alone or in conjunction with a film thickness gauge such as described in Wolbert, above-referenced, to overcome the deficiencies inherent in merely measuring average film thickness such as pointed out hereinabove.

DESCRIPTION OF THE DRAWINGS

Other objects and many of the attendant advantages of the present invention will be better appreciated and said invention will become clearly understood with reference to the following detailed description when considered in conjunction with the accompanying drawings illustrating one embodiment of the instant invention, wherein.

DETAILED DESCRIPTION OF THE INVENTION

Figure 1:
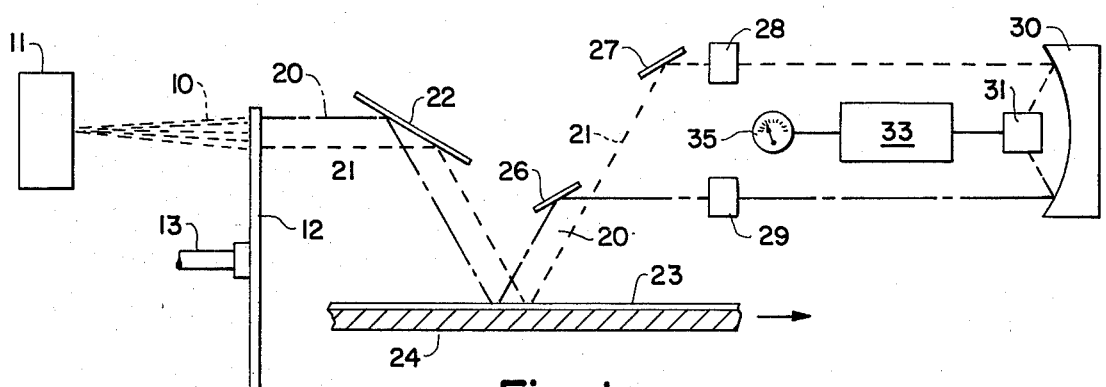
FIG. 1 provides a diagrammatic illustration of a prior art coating thickness gauge.

Referring to the drawings in more detail and, more particularly, to FIG. 1, a prior art coating thickness gauge is illustrated. Polychromatic infrared radiation is illustrated generally at 10 and emanates from a source such as an uncovered, electrically heated, platinum-rhodium winding installed in a polished cylindrical housing 11 of stainless steel having a properly located opening to direct the radiation into the desired channel. The radiation 10 strikes an interrupter or chopper generally designated 12, rotated at a constant speed on a shaft 13 by a suitable source of motive power not shown. The chopper 12 comprises a disc (not shown) which has portions of its periphery removed to form notches. Adjacent its unnotched periphery, the disc has arcuate slots (not shown) and the configuration of the chopper is well-known in the art and more fully described in Wolbert, supra. By rotating at a constant velocity in the path of the emitted radiation 10, the chopper 12 breaks this emitted radiation into two separate beams, the beam 20 and the beam 21 which, after optical filtration more fully described, infra, will become the reference beam and the sample beam, respectively. One beam is permitted to pass the chopper 12 by virtue of the notches whereas the other beam is transmitted through the slots with the transmission of each beam taking place intermittently and alternately with the other beam.

The two beams 20 and 21, traveling in parallel paths, strike an angularly disposed mirror 22 and are reflected downwardly toward a coating 23 to be measured and carried on the reflective surface of a moving sheet metal substrate 24. Each beam 20 and 21 passes through the coating 23, strikes the reflective surface and is reflected upwardly out of the coating. As will be pointed out infra, a portion of each of the beams 20 and 21 will also be reflected from the upper surface of the coating 23.

After their reflectance from the surface of the substrate 24 and their second passage through the coating 23, the beam 20 and the beam 21 strike angularly disposed mirrors 26 and 27, respectively; and are reflected through optical filters 28 and 29, respectively. The optical filters 28 and 29 remove from each beam all radiant energy of a wave length other than that desired, making each beam monochromatic and transforming them into the reference beam 20 and sample beam 21.

The reference beam 20 and the sample beam 21 strike a concave mirror 30 and are reflected intermittently into a detector 31. The detector 31 generates a small current according to the intensity of the infrared radiation of the reference beam 20 and the sample beam 21 striking it. The beams must strike the detector one at a time and alternately. This intermittent, alternate passage of the reference and sample beams is accomplished by the chopper 12, which also breaks the intermittent light into substantially single parallel beams in a well-known manner.

The voltage generated by the detector 31 is passed through an amplifier 33, whereupon it is amplified to a conveniently usable level and thereafter transmitted to a visual output device such as the meter 35.

Figure 2:
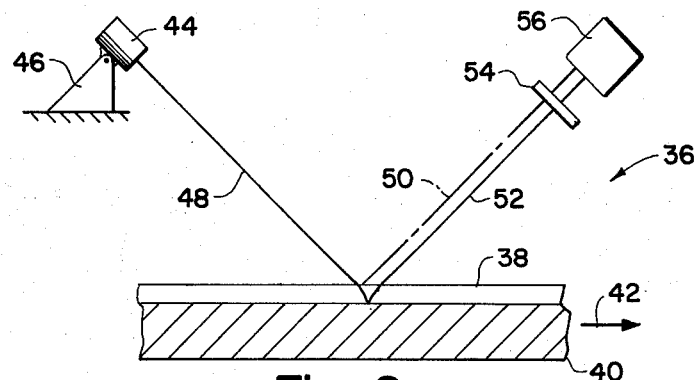
FIG. 2 provides a diagrammatic illustration of a uniformity monitoring system without polarimetric interference elimination.
Figure 3:
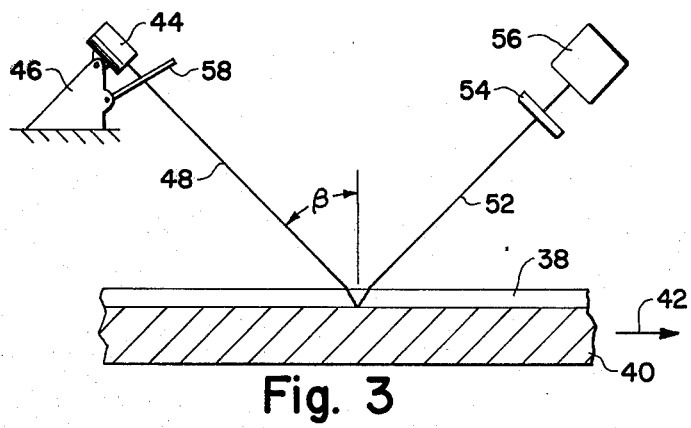
FIG. 3 provides a diagrammatic illustration of the optical system of FIG. 2 employing a transmission polarizer in the path of the radiation incident on the film and thereby eliminating optical interference.
Figure 4:
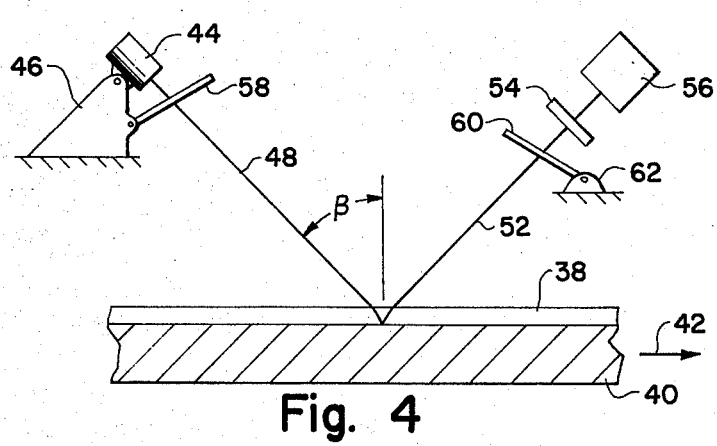
FIG. 4 provides a diagrammatic illustration of the apparatus of FIG. 2 employing transmission polarizers on both the incident beam of radiation on the film and the reflected beam of radiation on the film thereby eliminating optical interference.

Referring again to FIG. 2, a species of the present invention is illustrated generally at 36 and is illustrated in conjunction with a thin film or coating 38 supported on a reflective metal substrate such as an aluminum substrate 40. As best seen in FIGS. 2, 3 and 4, the film 38 and substrate 40 are indicated as moving in the direction of the arrow 42 at what in practice may be speeds on the order of 1,000 feet per minute. A source of polychromatic infrared radiation is indicated generally at 44 pivotally supported in a well-known manner as by a base 46 such that the angle of incidence between the radiation emanating from the source 44 with respect to the plane of the film 38 may be controlled as desired. Typically, the source 44 may comprise an electrically heated strip of nicron ribbon suitably supported or may be similar to that described in connection with the housing 11 of FIG. 1, supra. Polychromatic radiation emanating from the source 44 and directed toward the film 38 is illustrated generally at 48 and, as best illustrated in FIG. 2, a portion of the radiation 48 reaching the top surface of the film 38 is reflected therefrom as the beam 50. Similarly, a portion of the beam 48 reaching the top surface of the film 38 is transmitted therethrough and reflected from the interface between the film 38 and the substrate 40 back through the film 38 as the beam 52. The beams 50 and 52 are transmitted through a narrow band pass optical filter 54 designed to transmit a narrow band of infrared radiation having a wave length or frequency with respect to which the film 38 is absorptive such as radiation having a wave length of approximately 3.43 microns which is suitable for an exemplary organic coating for rigid container sheet. After passing through the filter 54 the radiation impinges on a detector such as the detector 56 (Pyroelectric IR Detector Model No. KT-2000 Series manufactured by Laser Precision Corporation and commercially available). The detector 56 provides an electrical output signal indicative of the uniformity or lack thereof of the film 38 and may be subsequently fed to a visual readout such as is common in the art.

In using a uniformity detector such as described, it is necessary to detect discontinuities in the direction of travel as small as ¼ inch. The imperfections or irregularities in the film 38 moving past the incident beam of radiation 48 will cause the amplitude of the output beam 52 to vary in intensity at a frequency which is the function of the size of the discontinuities or non-uniformities in the film 38, the spacing between such non-uniformities, the size of the optical "window" and the speed of the film in the direction 42. It is also desirable in many cases to cause the source of radiation 44 to traverse the film transversely of the direction of travel 42 to monitor a larger region of the surface of the film 38.

In practice because of the size and number of the non-uniformities in the film 38 and because of the speed of the film, optical interference taking place between the reflected beams 50 and 52 (due to their phase displacement by the film) may make it impossible in many instances to satisfactorily monitor film uniformity.

In an effort to minimize the optical interference caused by the unwanted reflection of the beam 50, reference may be had to the embodiments of FIGS. 3 and 4. To the extent that the components of FIGS. 3 and 4 are identical to those of FIG. 2, the same reference numerals have been used to designate corresponding parts. As seen in FIGS. 3 and 4, the source of polychromatic infrared radiation 44 is positioned with respect to its base 46 so as to direct the radiation 48 onto the film 38 at Brewster's Angle Beta. Furthermore, a transmission polarizer 58 is interposed between the source 44 and the film 38 and positioned with respect to the base 46 such that the beam 48 impinges on the surface of the polarizer 58 at Brewster's Angle for such polarizer 58. The effect of positioning the polarizer 58 at Brewster's Angle with respect to the beam 48 is such that the radiation 48 transmitted through the polarizer 58 will be plane polarized by eliminating the horizontal components thereof. When the plane polarized radiation 48 impinges on the film 38 at Brewster's Angle for the said film 38, it will be substantially transmitted through the film 38 and reflected from the interface between said film 38 and the aluminum substrate 40 as the beam 52. Inasmuch as the upper face of the film 38 can only reflect the horizontal component (parallel to the plane of the film 38) of the radiation 48 incident thereon at Brewster's Angle, and inasmuch as the radiation 48 is plane polarized so as not to contain the horizontal component, it should be clear that there will be no reflection from the upper surface of the film 38 in the form of a beam 50 as in FIG. 2. Consequently, optical interference errors inherent with the device of FIG. 2 will be substantially eliminated with the device of FIG. 3. It should be noted, however, that in practice the polarization effected by the polarizer 58 and the upper surface of the film 38 is not complete and there may be some undesired component reflected in the form of the undesired beam 50. In order to minimize any unwanted reflection from the upper surface of the film 38 resort may be had to the embodiment of FIG. 4. Essentially, the embodiment of FIG. 4 differs from that of FIG. 3 in incorporating a second transmission polarizer 60 which is pivotally secured to a support 62 in a well-known manner. The transmission polarizer 60 is interposed between the detector 56 and the film 38 in the path of the beam 52 reflected from the interface _f said film 38 and the substrate 40. The polarizer 60 is pivoted with respect to its support 62 so as to cause the beam 52 to be incident thereon at Brewster's Angle, whereby said polarizer 60 will only pass light whose plane of polarization contains the vertical component passed by the polarizer 58. However, some polarizing means are not restricted to disposition at Brewster's Angle. Thus, the polarizer 60 will block any residual reflected energy having a horizontal component such as the beam 50 of FIG. 2. It should be emphasized at this point that the polarizers 58 and 60 may take the form of any known transmission polarizing material, the selection of which is within the purview of those skilled in the art. Typically, however, the polarizers 58 and 60 may comprise germanium optical flats such as may be commercially obtained from Laser Precision Corporation.

It should now be evident that the problem inherent in the unwanted reflection of the beam 50 from the surface of the film 38 as is the case in the embodiment of FIG. 2 will also happen in a prior art device such as that of FIG. 1. Indeed in the embodiment of FIG. 1 such unwanted reflection will occur with respect to both the reference beam 20 and the sample beam 21. It should also be clear from this disclosure that the generic teachings of the subject invention can be also put to use in the coating thickness gauge of FIG. 1 by controlling the angle of incidence of the beams 20 and 21 on to the film 23 at Brewster's Angle and by suitably positioning transmission polarizers in the paths of the beams 20 and 21 either before or subsequent to their incidence and reflection, respectively, from the film 23. It should also be apparent from this disclosure that an additional polarizer may be used as is the case of the embodiment of FIG. 4 to thoroughly eliminate any residual unwanted reflection in the device of FIG. 1.

It can readily be seen that many variations and modifications of the present invention are possible in the light of the aforementioned teachings, and it will be apparent to those skilled in the art that various changes in form and arrangement of components may be made to suit requirements without departing from the spirit and scope of the invention. It is, therefore, to be understood that within the scope of the appended claims, the instant invention may be practiced in a manner otherwise than is specifically described herein.

What is claimed is:

1. A method of monitoring physical parameters of films or coatings having first and second at least partially reflective surfaces, including the steps of:
    directing a beam of optical radiation having at least a portion thereof which will be absorbed by the film onto said first surface at a predetermined angle so as to plane polarize any radiation reflected from said first surface and transmitting at least a portion of the radiation through said film to said second surface;
    reflecting the transmitted radiation from said second surface back through said film;
    transducing said radiation reflected from said second surface having a narrow band width with respect to which the film is absorptive to provide an output signal which is a function of absorption of said radiation by said film; and
    polarizing said radiation to be transduced to block any component of said radiation other than that transmitted through said film.

2. The method of claim 1, wherein said radiation directed onto said first surface is transmitted through a polarizing medium prior to reaching said first surface, thereby preventing at least a portion of said radiation reaching said first surface from being reflected therefrom.

3. The method of claim 1, wherein the radiation transmitted through said film is transmitted through a polarizing medium prior to transducing said radiation.

4. The method of claim 1, wherein said radiation directed onto said first surface is transmitted through a polarizing medium prior to reaching said first surface, thereby preventing at least a portion of said radiation reaching said first surface from being reflected therefrom and the radiation transmitted through said film is transmitted through a polarizing medium prior to transducing said radiation.

5. The method of claim 1, wherein said radiation is polarized by passing it through a polarizing medium which is so oriented that the radiation transmitted therethrough intercepts same at Brewster's Angle.

6. The method of claim 2, wherein said polarizing medium is so oriented that the radiation transmitted therethrough intercepts same at Brewster's Angle.

7. The method of claim 3, wherein said radiation transmitted through said polarizing medium intercepts same at Brewster's Angle.

8. The method of claim 1 which includes directing the radiation reflected from said second surface through a narrow band pass optical filter prior to transducing the radiation to select said narrow band width of radiation.

9. In a process for measuring parameters of films or coatings of the type wherein a beam of optical radiation having at least a portion thereof which will be absorbed by the film is directed onto a first surface of said film, partly reflected therefrom and partly transmitted through said film to a second surface and partly reflected therefrom, and a narrow band width of radiation having a wave length with respect to which the film is absorptive selected to be transduced for measuring the radiation absorbed by the film; said reflected radiation from said first and second surfaces being directed to transducing means; a method of preventing optical interference between said reflected radiation from said first and second surfaces, including the steps of:
    directing said beam of radiation onto said first surface at a predetermined angle such that any radiation reflected therefrom will be plane polarized in a given direction, and directing the beam of radiation at a polarizing medium oriented to pass radiation polarized in a direction different from said given direction to thereby prevent transmission of at least a portion of said radiation that would otherwise be reflected from said first surface.

10. The method according to claim 9, wherein said radiation directed onto said first surface is transmitted through said polarizing medium prior to reaching said first surface and said predetermined angle is Brewster's Angle.

11. The method pursuant to claim 9, wherein all radiation reflected from said film is directed toward said polarizing medium after the reflection thereof from said film.

12. The method as recited in claim 9, wherein said radiation directed onto said first surface is transmitted through a polarizing medium prior to reaching said first surface, thereby preventing at least a portion of said radiation reaching said first surface from being reflected therefrom, and all radiation transmitted through said film is transmitted through a polarizing medium prior to transducing said radiation.

13. The method of claim 9, wherein said polarizing medium is so oriented that the radiation transmitted therethrough intercepts same at Brewster's Angle.

14. The method according to claim 10, wherein said polarizing medium is so oriented that the radiation transmitted therethrough intercepts same at Brewster's Angle.

15. The method as recited in claim 11, wherein said radiation transmitted through said polarizing medium intercepts same at Brewster's Angle.

16. A method of monitoring the thickness uniformity of a thin film or coating having at least a partially reflective first surface and a partially reflective second surface, including the steps of:
- scanning said film with a continuous beam containing radiation of a wave length with respect to which said film or coating is absorptive, and which is directed onto said first surface at a predetermined angle such that any light reflected from said first surface will be plane polarized in a first direction;
- transmitting said scanning beam through a polarizing medium positioned to intercept said scanning beam at a predetermined angle and plane polarize the same in a direction different from said first direction;
- moving said film past said scanning beam;
- reflecting a portion of the radiation incident on said first surface from said second surface and back through said first surface;
- selecting radiation of a narrow band width with respect to which said film is absorptive; and
- transducing said narrow band width of radiation reflected by said second surface and transmitted through said first surface to thereby provide an output signal indicative of the thickness uniformity of said film.

17. Apparatus for monitoring physical parameters of films or coatings having first and second at least partially reflective surfaces, including:
- means for directing a beam of optical radiation having at least a portion thereof which will be absorbed by the film onto said first surface at a predetermined angle so as to plane polarize any radiation reflected from said first surface of said film;
- means for selecting a narrow band width of radiation with respect to which the film is absorptive;
- means for receiving and transducing said narrow band width of radiation reflected from said second surface to provide an output signal as a function of a parameter of said film; and
- polarizing means positioned to intercept all of said radiation reaching said transducing means so as to block any component of said radiation other than that transmitted through said film, thereby preventing optical interference with said radiation reflected from said second surface by radiation reflected from said first surface.

18. The apparatus of claim 17 wherein said polarizing means is positioned between said beam directing means and said first surface such that the radiation directed onto said first surface is transmitted through said polarizing means prior to reaching said first surface, thereby preventing at least a portion of said radiation reaching said first surface from being reflected therefrom.

19. Apparatus according to claim 17, wherein said polarizing means is interposed between said first surface and said transducing means such that all radiation reflected from said film will be transmitted to said polarizing means prior to reaching said transducing means.

20. The invention pursuant to claim 17, wherein said polarizing means is positioned between said first surface and said beam directing means such that the radiation directed onto said first surface will be plane polarized so as to prevent at least a portion thereof from being reflected from said first surface; and further including additional polarizing means interposed between said first surface and said detecting means to prevent any residual light reflected from said first surface reaching said transducing means.

21. The apparatus as recited in claim 17, wherein said polarizing means is so oriented that the radiation transmitted therethrough intercepts same at Brewster's Angle.

22. The invention as delineated in claim 18, wherein said polarizing medium is so oriented that the radiation transmitted therethrough intercepts same at Brewster's Angle.

23. The apparatus of claim 19, wherein said polarizing means is oriented to intercept the radiation reflected from said film at Brewster's Angle.

24. The invention as recited in claim 20, wherein both said polarizing means and said additional polarizing means are oriented at Brewster's Angle with respect to their received beams of radiation.

25. An apparatus for measuring parameters of films or coatings of the type wherein a beam of optical radiation having at least a portion thereof which will be absorbed by the film is directed onto a first surface of said film, partly reflected therefrom and partly transmitted through said film to a second surface and partly reflected therefrom, and a narrow band width of radiation having a wave length with respect to which the film is absorptive selected to be transduced; said reflected radiation from said first and second surfaces being directed to transducing means; apparatus for preventing optical interference between reflected radiation from said first and second surfaces, including:
- means for directing said beam of radiation onto said first surface at a predetermined angle such that any radiation reflected therefrom will be plane polarized in a given direction; and
- means for polarizing all radiation otherwise reflected from said first surface in a direction different from said given direction.

26. The invention pursuant to claim 25, wherein said polarizing means is positioned between said first surface and said beam directing means and said predetermined angle is Brewster's Angle.

27. Apparatus according to claim 25, wherein said polarizing means is positioned between said first surface and said transducing means.

28. Apparatus as recited in claim 25, wherein said polarizing means includes a first polarizing medium positioned between said first surface and said beam directing means such that the radiation directed onto said first surface is transmitted through said first polarizing medium prior to reaching said first surface, thereby preventing at least a portion of said radiation reaching said first surface from being reflected therefrom; and said polarizing means further includes a second polarizing medium positioned between said first surface and said transducing means such that all radiation reflected from said film is directed at said second polarizing medium prior to reaching said transducing means.

29. Apparatus for monitoring the thickness uniformity of a thin film or coating moving past a work station at a predetermined rate and having at least a partially reflective first surface and a partially reflective second surface, including:

means for scanning said first surface with a continuous beam containing radiation of a wave length with respect to which said film is absorptive;

means for directing said scanning beam onto said first surface at a predetermined angle such that any light reflected from said first surface will be plane polarized in a first direction;

polarizing means positioned to intercept said scanning beam at a predetermined angle and plane polarize same in a direction different from said first direction;

filter means for transmitting only radiation of a narrow band width with respect to which the film is absorptive; and transducing means for receiving at least a portion of the radiation reflected by said second surface and transmitted through said first surface to thereby provide an output signal indicative of the thickness uniformity of said film.

30. Apparatus for monitoring thickness uniformity of coatings or the like moving past a station at a controlled speed, and having first and second at least partially reflective surfaces; including:

means for directing a continuous beam of infrared radiation onto said first surface at such an angle that any radiation reflected from said first surface will be plane polarized in a first direction;

means for selecting a narrow band width of radiation having a wave length with respect to which said coating is absorptive;

at least a portion of said continuous beam being transmitted to said second surface and being reflected therefrom through said first surface; and transducing means for receiving radiation of said narrow band width reflected from said coating or the like and providing an output signal indicative of the thickness uniformity of the coating or the like.

31. Apparatus pursuant to claim 30, further including first polarizing means positioned in the path of said scanning beam between said coating or the like and said beam directing means, for plane polarizing said scanning beam in a direction normal to said first direction.

32. Apparatus as set forth in claim 30, further including first polarizing means positioned in the path of the radiation reflected from said coating or the like, between said coating or the like and said transducing means, for plane polarizing said reflected radiation in a direction normal to said first direction.

33. The invention as related in claim 31, further including second polarizing means positioned in the path of the radiation reflected from said coating or the like, between said coating or the like and said transducing means, for plane polarizing said reflected radiation in said direction normal to said first direction.

34. The invention pursuant to claim 31, wherein said first polarizing means comprises an optical flat transparent to infrared radiation oriented at Brewster's Angle with respect to its transmitted radiation.

* * * * *

Disclaimer 4,015,127.—*Allen J. Sharkins*, Lower Burrell, Pa. MONITORING FILM PARAMETERS USING POLARIMETRY OF OPTICAL RADIATION. Patent dated Mar. 29, 1977. Disclaimer filed June 5, 1978, by the assignee, *Aluminum Company of America*.

Hereby enters this disclaimer to all claims of said patent.

[*Official Gazette July 18, 1978.*]